United States Patent [19]
Brunke et al.

[11] Patent Number: 5,260,459
[45] Date of Patent: Nov. 9, 1993

[54] CYCLIC ISOLONGIFOLANONE-KETALS - THEIR MANUFACTURE AND THEIR APPLICATION

[76] Inventors: Ernst-Joachim Brunke, Pippingsbusch 3, Holzmimden, 3450; Dietmar Schatkowski, Weststrasse 7, Stadtoldendorf 3457, both of Fed. Rep. of Germany

[21] Appl. No.: 978,239

[22] Filed: Nov. 18, 1992

[30] Foreign Application Priority Data

Nov. 19, 1991 [DE] Fed. Rep. of Germany ......... 413832

[51] Int. Cl.⁵ .......................................... C07D 317/92
[52] U.S. Cl. .................................................... 549/336
[58] Field of Search ........................................ 549/336

[56] References Cited

U.S. PATENT DOCUMENTS

| | | | |
|---|---|---|---|
| 3,887,622 | 6/1975 | Boelens et al. | |
| 4,331,569 | 5/1982 | Inoue et al. | 549/336 |
| 4,774,225 | 7/1988 | Giraudi | 549/336 |
| 4,841,075 | 6/1989 | Matsushita et al. | 549/336 |

FOREIGN PATENT DOCUMENTS 2336798  1/1974  Fed. Rep. of Germany.
1505821  3/1978  United Kingdom.

OTHER PUBLICATIONS

CA 81(5): 25442f (1974).
CA 89(7): 59977g (1978).

*Primary Examiner*—Marianne M. Cintins
*Assistant Examiner*—John Peabody
*Attorney, Agent, or Firm*—Dominik, Stein, Saccocio, Reese, Colitz & Van der Wall

[57] ABSTRACT

The cyclic Isolongifolanone ketals of the general formula A wherein the wavy lines mean α and β-configuration and R,R' mean radicals of hydrogen, methyl or ethyl, are new. With preference they are used either as odorants or as components of perfume compositions. They are manufactured from Isolongifolene which is itself produced from Longifolene as is well known. Isolongifolene is oxydized to Isolongifolene-3-on and this is reacted with aliphatic 1,2-diols in apolar solvents with the separation of water.

6 Claims, 1 Drawing Sheet

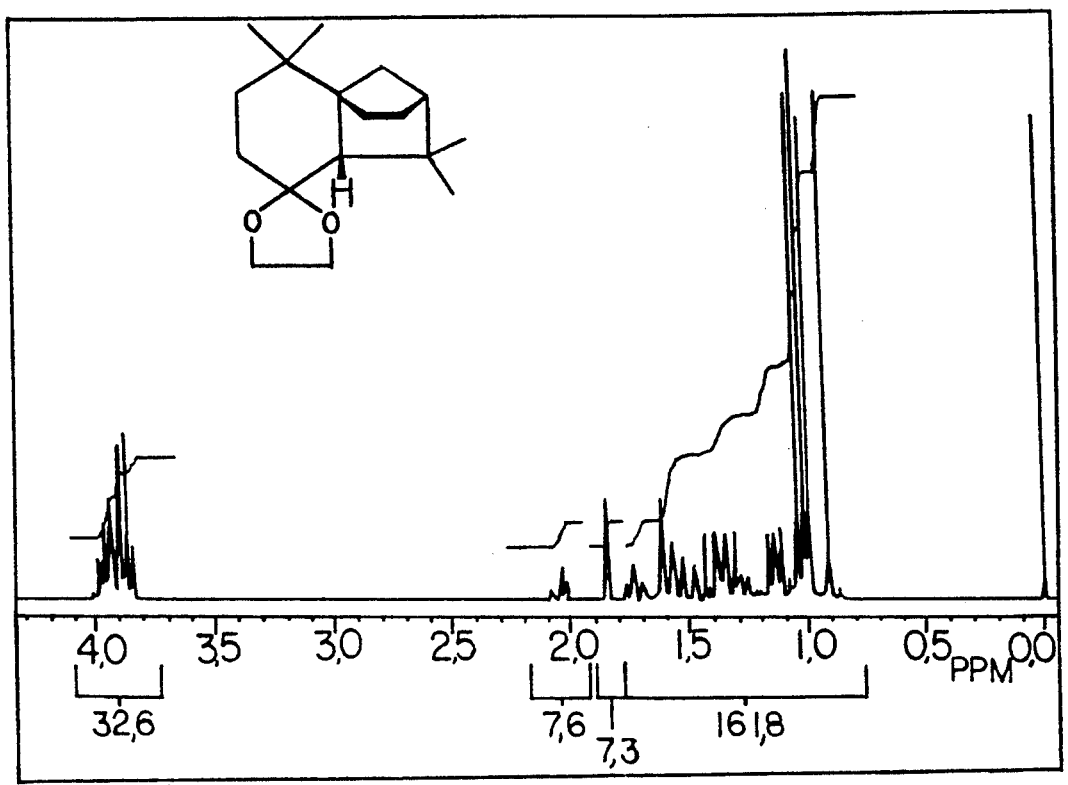
FIG. 1 ¹H-NMR-SPECTRUM (300 MHz, CDCL₃) OF 5a
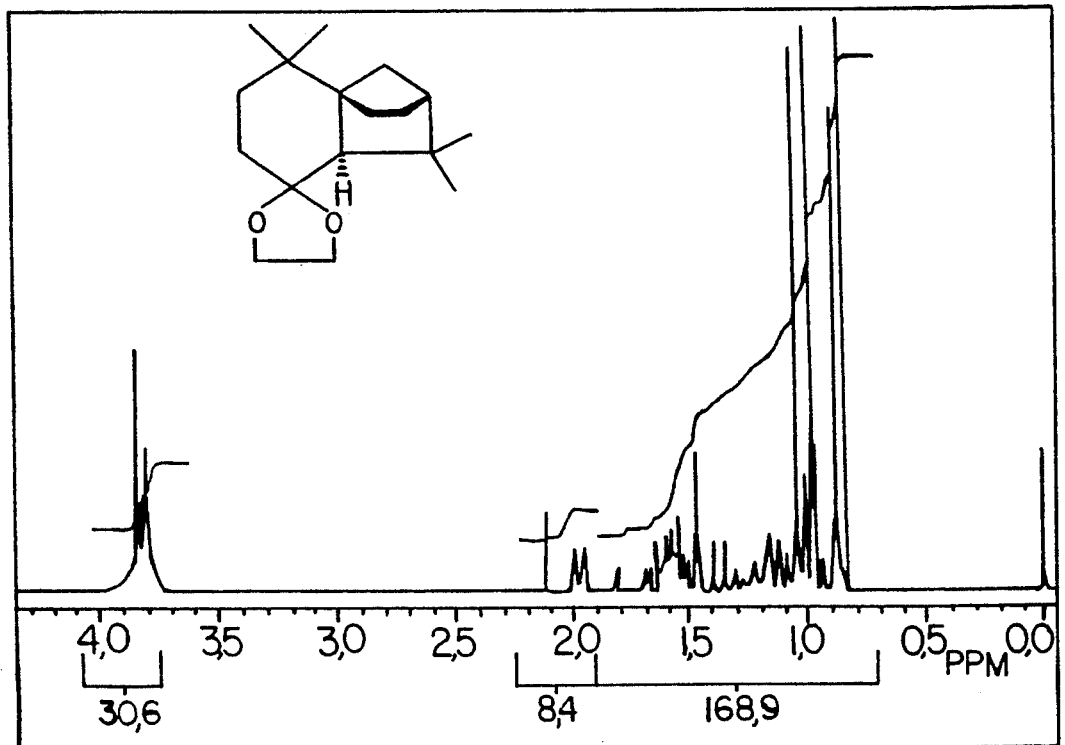
FIG. 2 ¹H-NMR-SPECTRUM (300 MHz, CDCL₃) OF 5b

CYCLIC ISOLONGIFOLANONE-KETALS - THEIR MANUFACTURE AND THEIR APPLICATION

Today, industrially manufactured perfume oils consist of synthetic odorants largely. The traditional application of essential oils or extracts of vegetable or animal origin is now mainly restricted to the area of alcoholic perfumery. Perfume for detergents, soaps, household cleaners and similar products requires the use of odorants which meet the technical demands of stability and substantivity. To comply with these demands, perfumes which are used in technical consumer products are essentially composed of synthetic odorants. Because these perfume oils are needed in large quantities as a result all major perfume companies and manufacturers of aroma chemicals have dedicated their research work over the last decades to produce new aroma chemicals.

It has become increasingly apparent during the last 10 years that synthetic odorants which were originally destined for the technical perfumery, and which due to their low prices and high stability were accordingly positioned in the market are now more and more used in the alcoholic perfumery. Perfumers have used their perfumistic know-how gained from the use of synthetic aroma chemicals in technical perfumes and applied it also to alcoholic perfumery as aesthetic chances may allow. Today, a sucessfull new aroma chemical has to meet the following demands:

1. it has to present a high olfactory and aesthetic value and must be applicable in as wide a range of fragrance products as possible;
2. it has to be stable in most technical applications;
3. it has to show a good value-/for money-ratio;
4. it should be manufactured from generally available raw materials from renewable resources, whenever possible.

Such a raw material of natural origin available in large quantities is Longifolene (1) which is to be found as a main component in the Indian oil of turpentine and as a minor component in many other turpentine oils and other essential oils.

About 20 years ago, research laboratories of the aroma chemical industry produced a number of derivative products from Longifolene, which had odorant qualities. As reported in a summary by G. Ohloff in his book "Riechstoffe und Geruchssinn" (Springer-Verlag, Berlin, 1990, ISBN-Nr. 3-540-52560-2, pages 87-88) at least 4 commercial odorants are derived from the Longifolene (1). The Isolongifolene (2) which is obtained by the isomerization of Longifolene (1) can be proved to have fathered 13 commercial products. The chemistry and olfactory qualities of derivates of the Isolongifolene (2) are summarized by G. Färber and H. Tan:

"Riechstoffe aus Isolongifolen", G. Färber, Parfü merie & Kosmetik, 68, 18 (1987)

"Der Gebrauch von Riechstoffen aus Isolongifolenen in der Parfümerie", H. Tan, Parfümerie & Kosmetik, 67, 564 (1986)

The derivates of Isolongifolene (2) obtained by epoxidation, Prins-reaction (reaction with formaldehyde) or allylic oxidation are considered olfactorily more valueable than the derivates of Longifolene (1). They (2) are odorants of a warm-woody odor type, with some little amberlike aspects (Ohloff loc. cit.).

The epoxide (3) obtained by the reaction of Isolongifolene with peracids can be transferred as is known into mixtures of epimer ketones. The ketone mixtures may contain different proportions of isomers with different odor effects. The ketone 4a is preferably manufactured in kinetic reaction while the ketone 4b is the thermodynamically more stable epimer.

According to the state of the art as described above, this area of the aroma chemical chemistry is considered to be especially well researched. Together with the derivates of Longifolene and Isolongifolene which have useful odor qualities, a large number of other derivates are known with little or no such value.

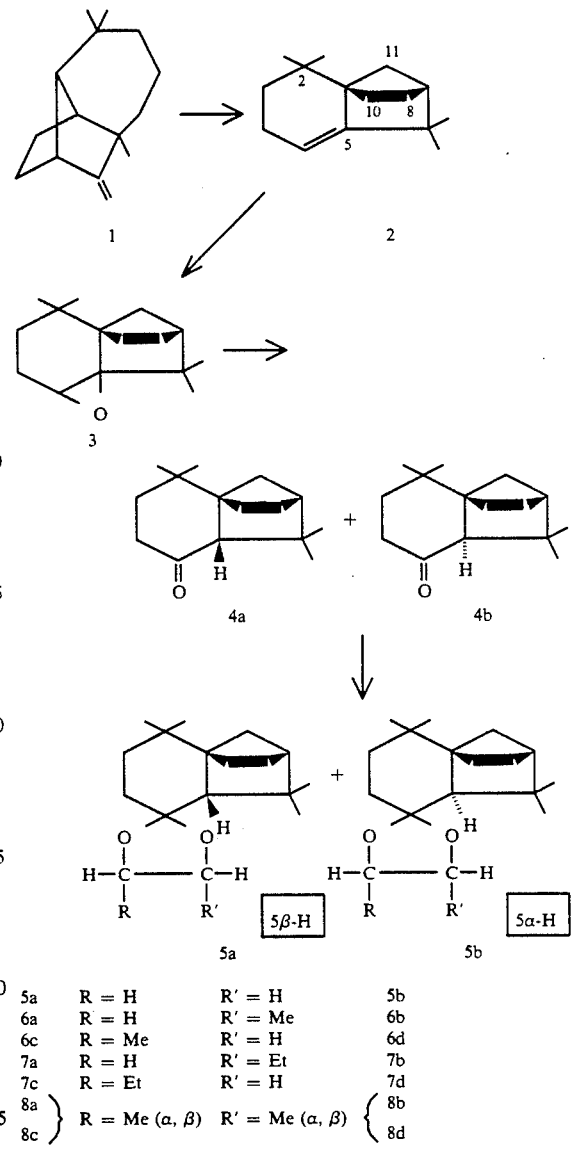

| | R = H | R' = H | |
|---|---|---|---|
| 5a | R = H | R' = H | 5b |
| 6a | R = H | R' = Me | 6b |
| 6c | R = Me | R' = H | 6d |
| 7a | R = H | R' = Et | 7b |
| 7c | R = Et | R' = H | 7d |
| 8a } | R = Me (α, β) | R' = Me (α, β) | { 8b |
| 8c } | | | { 8d |

It is all the more surprising therefore, that new valuable odorants could be found in the area of the Longifolene derivates such as the herewith claimed new cyclic acetals of the general formula A. The acetals of the general formula A present unique olfactory qualities clearly standing out from the known odorants derivated from Isolongifolene (2) and superior to them. The new compounds of the general formula A present strongly woody olfactory qualities with flowery-fresh effects and with a velvety moss/ambra accent (see example 1); they are especially longlasting and act as fixatives.

For the manufacture of compounds of the general formula A, Longifolene (1) has been treated as is well known with a mixture of acetic acid and sulphuric acid [U. R. Nayak, S. Dev, Tetrahedron 8, 42–48 (1960)] or with bortrifluorid-etherate [R. E. Beyler, G. Ourisson, J.Org.Chem. 30, 2838–2839 (1965)] to obtain Isolongifolene (2) by isomerization. The epoxide (3) [L. K. Lala, J. B. Hall, J.Org.Chem. 35, 1172, (1970); J. R. Prahlad, R. Ranganathan, W. Ramdas Nayak, T. S. Santhanakrishnan, S. Dev, Tetrahedron Lett. 8, 417 (1964)] obtained by epoxidation of Isolongifolene (2) has been transformed, as is well known, into the mixture of the epimer ketones 4a/4b [R. Ranganathan, U. R. Nayak, T. S. Santhanakrishnan, S. Dev, Tetrahedron 26, 621 (1970)]. In known conditions of the kinetic reaction the ring-opening of the epoxide produced a mixture of ketones 4a/4b concentrated in 4a (see example 2=96:4). It is known that 4a will be isomerized into the thermodynamically more stable ketone 4b under the influence of basic catalysts or by heating. Depending on the conditions of the reaction, mixtures of equilibrium of 4a/4b are obtained [L. K. Lala, J. Org. Chem. 36, 2560–2561 (1971)].

Our example 3 shows an isomerization not yet described to date leading from a mixture of ketones 4a/4b (96:4) to a specially highly concentrated mixture of equilibrium 4a/4b (9:91). The ketones 4a/4b have been isolated by distillation and chromatography and spectroscopically characterized. [C. W. Greengrass, R. Ramage, Tetrahedron 31, 689–694 (1975)].

From ketones 4a, 4b which were present purely or in high concentration or in mixtures of equilibrium the new cyclic acetales of the formula A are produced as is known by the reaction with aliphatic 1,2-dioles in acidic catalysis with separation of water. The separation of water is preferably realized at boiling point with suitable inert solvents as carriers (examples 5–10).

If different solvents—toluene, cyclohexane, benzene fractions or n-pentane—are applied, the epimer ketals are produced in different proportions (example 5). So from 4a/4b (86:14) in example 2 under the effect of ethylene glycol in toluene the ketals 5a/5b have been obtained in the ratio of 3:2. When using n-pentane a ketal mixture 5a/5b was obtained after even a markedly prolonged reaction period. The ketals of formula A can be separated alternatively by distillation of the starting material 4a/4b if need be.

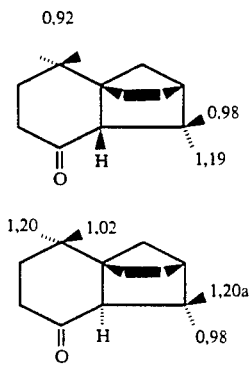

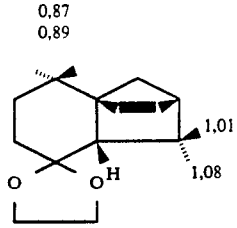

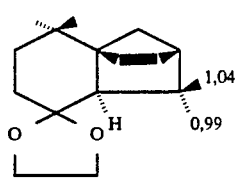

1H-NMR-Data, δ[ppm]

The mixture equilibrated by basic catalysis of ketones 4a/4b (9:91, in example 3) had to undergo ketalisation reactions as well. Depending on the solvent used, different mixtures of 5a/5b were obtained, but which differed from the ketal mixtures 5a/5b obtained from the ketone mixtures 4a/4b (86:14, of example 2) so far as their relative concentrations were concerned. This varying reaction may be understood as kinetically controlled reaction during during the ketalisation.

Analogues to the ketals 5a/5b the ketals 6a/6b/6c/6d were obtained by reaction of 4a/4b with 1,2-propandiol, the ketals 7a/7b/7c/7d with 1,2-butandiol, the ketals 8a/8b/8c/8d with 2,3-butandiol - each of them as a mixture. The methyl- or ethyl groups of the ketal radical may appear in an o- or B-configuration.

The compounds 5a, 6a, 6c, 7a, 7c, 8a, 8c are established as 5β-configurated; the compounds 5b, 6b, 6d, 7b, 7d, 8b, 8d as 5a-configurated. Because starting from (+)-Longifolene the chiral ketals of the general formula A were obtained by means of the chiral ketones 4a/4b; 4a/4b exist as a mixture of epimers (5a/5b), respectively as diastereo isomers. 6a/6b and 7a/7b are constitutionally isomer to 6c/6d, respectively 7c/7d. Starting from (−)Longifolene each of the enantiomer compounds 5a,b–8a–d are accessable.

Since both the composition of the ketal mixtures depends on the conditions of the reaction (example 5), and, the single diastereo isomers may be obtained in purity (examples 6, 7), the proportions within the mixtures may be adjusted to any level.

The attribution of the structure of the new compounds 5–8 has been based on the spectroscopical results (examples 5–10). The 1H-NMR-spectra of the compounds 5a, 5b (designs 1, 2) have been interpreted in analogy to the attributions given by C. W. Green-grass and R. Ramage, Tetrahedron 31, 689 (1975B) for the ketones 4a, 4b.

The new compounds of the formula A are well suited as odorants due to their olfactory qualities and their stability. They may be used successfully for perfume compositions of any fragrance type either as a main component or in traces to good avail. The examples quoted may not be understood as limitations.

EXAMPLE 1

Manufacture of Isolongifolene (2)

Over a period of 30 minutes 240 g (0.79 mol) of Longifolene (1) (80% ex Indian oil of turpentine $[\alpha]_D + 39.4°$) were dropped into a heated solution (60° C.) of 90 g toluene and 10 g (0.07 mol) BF$_3$-etherate. This was stirred at 100° C. for 3 hours, than cooled down to room temperature and neutralized. After drying above Na$_2$SO$_4$ the solvent was distilled at reduced pressure. A raw product of 198 g (of 70.2% according to GLC) remained.

Gas chromatogram (HP 5890, DBWAX-30 N, 30 m, 150° C.–240° C., 8° C./min).

EXAMPLE 2

Manufacture of an Isolongifolanene mixture 4a/4b (86:14)

A threeneck-roundbottom-flask with jacketed coil condenser and dropping funnel was charged with 198 g (0.68 mol) Isolongifolene (2) (70.2% according to GLC) from example 1 plus 80 g toluene and 68 g (1.48 mol) formic acid and heated at 60°–70° C. Into this was dropped over a period of 1 hour 136 g (1.4 mol) H$_2$O$_2$ at 35% concentration. After stirring for 3 hours at 80°–85° C. it was cooled to room temperature and worked up. The separated organic phase was neutralized with sodium carbonate solution and water, dried above Na$_2$SO$_4$ and the solvent distilled at reduced pressure. 199 g raw product remained. GLC 4a (71%), 4b (2.5%) [96:4].

Distillation with a 15 cm Vigreux-column produced 165 g raw product of 4a/4b; b.p. 2 mm 120°–153 C. GLC: 4a (74%), 4b (3%).

A subsequent distillation with a column with metallic packing produced: 110 g 4a/4b (74.4% theoretical yield) b.p. 2 mm 137°–141° C.; GC 4a (77%), 4b (12.8%) [86:14].

D 20/4 = 1,0037
n 20/D = 1,5006
$[\alpha]$20/D = $-8,5°$

Gas Chromatogram: Conditions See Example 1
GLC/MS: HP 5970 DBWAX-60 N 60 m 60°–240° C. 4°/min 4a RT=40,47'
MS: m/e (%)=220 (100, M$^+$), 205 (41), 191 (82), 177 (41), 164 (62), 149 (50), 121 (56), 107 (40), 83 (27), 55 (21), 41 (17). 4b Rt=41,41'
MS: m/e (%)=220 (69, M$^+$), 205 (23), 191 (55), 177 (44), 164 (100), 149 (55), 121 (53), 107 (37), 91 (21), 55 (21), 41 (19).

EXAMPLE 3

C-3-Epimerization of Isolongifolanone (4a/4b)

880 g (4 mol) raw (undistilled) ketone mixture 4a/4b from example 2 (purity according to GLC: 4a (63.3%), 4b (2.48%) [96:4]; 750 g methanol, 40 g (0.5 mol) NaOH 50% were charged into a three-neck-roundbottom-flask and stirred for 8 hours under reflux. After this period 30 g (0.5 mol) concentrated acetic acid were added to cool down to room temperature. After the distillation of the solvent at reduced pressure the residual was mixed with water. The organic phase was then separated. The waterphase was extracted with 100 ml benzene. The mixed organic phases were washed first with sodium carbonate solution, then with water and dried above Na$_2$SO$_4$. The solvent was distilled at reduced pressure. 860 g dark brown oil remained.

GLC: 4a (6.3%), 4b (59.3%) [9:91]

EXAMPLE 4

C-3-Epimerization of pure Isolongifolanone (4a/4b)

440 g (2 mol) purely distilled ketone mixture 4a/4b from example 2 [purity according to GLC: 4a (77%), 4b (12.8%) [86:14]; 400 ml methanol, 20 g (0.25 mol) NaOH 50% were charged into a 2 l three-neck-roundbottom-flask and stirred for 5 hours under reflux. After cooling to room temperature, 15.5 g (0.25 mol) concentrated acetic acid were added; the solvent was distilled at reduced pressure. The residual was then mixed with water. The organic phase was separated and the water phase was extracted with 100 ml benzene. The mixed organic phases were neutralized with sodium carbonate solution and water; after concentration 430 g brown oil remained.

GLC: 4a (9.2%), 4b (79.5%) [1:9]

Distillation in a 15 cm Vigreux-column produced 411 g 4a/4b (b.p. 2 mm 135°–157° C.). The subsequent distillation in a 40 cm column with metallic packing produced 399 g (90.7% theor. yield) 4a/4b b.p. 2 mm 139°–142° C.

GLC: 4a (13.4%), 4b (80.6%) [14:86]
D 20/4 = 1.0042
n 20/D = 1.5007
$[\alpha]$ 20/D = $-34.7°$

EXAMPLE 5

Reaction of Isolongifolanone 4a/4b with ethylene glycol 220 g (0.6 mol) ketone mixture 4a/4b from example 2, 3 or 4, 186 g (3 mol) ethylene glycol, 1 g p-toluene sulfonic acid plus 300 ml solvent (toluene, cyclohexane, benzene (63°–80° C.), n-pentane) were charged in a 1 l three-neck-roundbottom-flask with water separator and heated at boiling point for 48–78 hours and stirred with water separation. During the reaction about 20 ml water each were separated at each stage. After cooling to room temperature, the mixture was neutralized with sodium carbonate solution and water, dried above Na$_2$SO$_4$, and the solvent distilled at reduced pressure 245–265 g raw product of either yellow or brown oil respectively were obtained.

Distillation with a 15 cm Vigreux-column produced 230 g raw 4a/4b (b.p. 2 mm 68°–170° C.). The subsequent distillation with a 40 cm column with metallic packing produced about 140 g (53% theor. yield) 5a/5b of light yellow oil.

Table 1 shows the results in a summary.

TABLE 1

| | Products of the reaction of 4a/4b with ethylenglycol/p-toluenesulfonic acid | | | | | | | | | | |
|---|---|---|---|---|---|---|---|---|---|---|---|
| | starting material (GLC-%) | | | | | Reaction | | Composition of Product (GLC-%) | | | |
| | a | + | 4b | [4a/4b] | Solvents | Temp. | Time | 4a | 4b | 5a | 5b | [5a/5b] |
| a) | 71% | | 2.5% | [96:4] | Benzene (63–80° C.) | 70–72° C. | 70 h | 7.2 | 3.8 | 53.6 | 2.2 | [96:4] |
| | 71% | | 2.5% | [96:4] | Cyclohexane | 90–92° C. | 48 h | 5.1 | 4.8 | 51.3 | 3.8 | [93:7] |
| | 71% | | 2.5% | [96:4] | Toluene | 120° C. | 24 h | 1.2 | 10.4 | 37.8 | 19.6 | [66:34] |
| | (raw products from example 2) | | | | | | | | | | |
| b) | 77% | | 12.8% | [86:14] | n-Pentane | 46–48° C. | 84 h | 17.1 | 11.1 | 60.1 | 0.8 | [99:1] |

TABLE 1-continued

<table>
<tr><th colspan="5">Products of the reaction of 4a/4b with ethyleneglycol/p-toluenesulfonic acid</th><th colspan="2">Reaction</th><th colspan="5">Composition of Product (GLC-%)</th></tr>
<tr><th colspan="2">starting material (GLC-%)</th><th></th><th>[4a/4b]</th><th>Solvents</th><th>Temp.</th><th>Time</th><th>4a</th><th>4b</th><th>5a</th><th>5b</th><th>[5a/5b]</th></tr>
<tr><td></td><td>77%</td><td>12.8%</td><td>[86:14]</td><td>Benzene (63–80°C.)</td><td>70–72° C.</td><td>72 h</td><td>1.8</td><td>14.6</td><td>57.9</td><td>14.3</td><td>[80:20]</td></tr>
<tr><td></td><td>77%</td><td>12.8%</td><td>[86:14]</td><td>Cyclohexane</td><td>90–92° C.</td><td>25 h</td><td>2.4</td><td>10.0</td><td>65.5</td><td>11.3</td><td>[85:14]</td></tr>
<tr><td></td><td>77%</td><td>12.8%</td><td>[86:14]</td><td>Toluene</td><td>120° C.</td><td>25 h</td><td>—</td><td>—</td><td>84.6</td><td>14.3</td><td>[86:14]</td></tr>
<tr><td colspan="4">(Distillate from example 2)</td><td></td><td></td><td></td><td></td><td></td><td></td><td></td><td></td></tr>
<tr><td>c)</td><td>6.3%</td><td>59.3%</td><td>[9:91]</td><td>Benzene (63–80° C.)</td><td>70–72° C.</td><td>78 h</td><td>1.2</td><td>14.5</td><td>28.6</td><td>19.8</td><td>[59:41]</td></tr>
<tr><td></td><td>6.3%</td><td>59.3%</td><td>[9:91]</td><td>Cyclohexane</td><td>90–92° C.</td><td>78 h</td><td>2.1</td><td>11.5</td><td>36.9</td><td>13.6</td><td>[73:27]</td></tr>
<tr><td></td><td>6.3%</td><td>59.3%</td><td>[9:91]</td><td>Toluene</td><td>120° C.</td><td>78 h</td><td>2.9</td><td>8.4</td><td>37.7</td><td>13.3</td><td>[73:27]</td></tr>
<tr><td colspan="4">(from example 3)</td><td></td><td></td><td></td><td></td><td></td><td></td><td></td><td></td></tr>
<tr><td>d)</td><td>13.4%</td><td>80.6%</td><td>[14:86]</td><td>Benzene (63–80° C.)</td><td>70–72° C.</td><td>72 h</td><td>—</td><td>22.9</td><td>35.6</td><td>35.1</td><td>[50:50]</td></tr>
<tr><td></td><td>13.4%</td><td>80.6%</td><td>[14:86]</td><td>Toluene</td><td>120° C.</td><td>48 h</td><td>1.5</td><td>3.3</td><td>67.9</td><td>19.8</td><td>[77:23]</td></tr>
<tr><td colspan="4">(from example 4)</td><td></td><td></td><td></td><td></td><td></td><td></td><td></td><td></td></tr>
</table>

EXAMPLE 6

Manufacture of 5-ethylenedioxy-3β-H-isolongifolane (5a)

20 g purified ketale mixture from example 5b; (purity according to GLC: 5a (84.6%), 5b (14.3%) [86:14], were distilled once more for purification in a 1 m spinning band column. 2.8 g 5a as a light yellow oil were obtained, b.p. 2 mm 142°–143° C.

GLC: 5a (98%), 5b (0,8 ) [99:1]
D 20/4 = 1,0510
n 20/D = 1,5051
GLC/MS: Conditions see example 2
5a RT 42.94'
MS: m/e (%) = 264 (23, M+), 249 (9), 235 (19), 195 (20), 165 (23), 127 (42), 99 (100), 55 (10).
$^1$H-NMR: see design 1
$^{13}$C-NMR (CDCl$_3$), Varian VXR-300): δ [ppm] = 21.86, 23.39, 26.79, 33.89 (CH$_3$), 21.06, 25.75, 32.76, 35.89, 37.95, 61.84, 63.71 (CH$_2$), 48.94, 52.48 (CH), 33.21, 37.67, 56.42, 112.23 (C).

EXAMPLE 7

Isolation of 5-ethylenedioxy-3α-H-isolongifolane (5b)

1 g of raw ketal mixture from example 5d (purity according to GLC: 5a (35.6%), 5b (35.1% [1:1]) was purified by repeated (3×) flash-chromatography.

Conditions of Chromatography 150 g silica gel 60, Grain size 0.04–0.063 mm,.(Merck, Art.-No. 9385).
Solvent Benzene/Ethyl acetate = 95/5
Weight: 1 g
Yield: 78 mg; GLC: 5a (3%), 5b (90%) [3:97]

GLC/MS: Conditions See Example 2

5b RT 44,67'
MS: m/e (%) = 264 (9, M+), 249 (1), 235 (1), 221 (2), 191 (1), 149 (2), 127 (9), 99 (100), 55 (6), 41 (3).
$^1$H-NMR: see design 2
$^{13}$C-NMR (CDCl:), Varian VXR-300): δ [ppm] = 25.51, 26.72, 26.93, 31.09 (CH$_3$), 26.01, 30.41, 31.65, 36.90, 37.56, 61.38, 63.05 (CH$_2$), 49.53, 56.89 (CH), 32.46, 40.99, 56.63, 111.78 (C).

EXAMPLE 8

Manufacture of 5-(1'-Methylethylenedioxy)-isolongifolane 6a/6b/6c/6d 440 g (2 mol) of purified ketone mixture 4a/4b from example 2; (purity according to GLC: 4a (77%), 4b (12.8%) [86:14], 760 g (10 mol) propylene glycol-1.2, 600 ml toluene, 2 g p-toluene sulfonic acid were charged into a 4 l three-neck-roundbottom-flask with water separator. The mixture was stirred for 30 hours under reflux. After cooling to room temperature it was neutralized with sodium carbonate solution and water, dried above Na$_2$SO$_4$ and the solvent was distilled at reduced pressure. 540 g of light brown raw product remained.

Distillation with a 15 cm Vigreux-column produced 298 g (53.6% theor. yield) 6a/6b/6c/6d; b.p. 2 mm 158°–162° C.).

GLC/MS: Conditions See Example 2

RT 41.11'
MS: m/e (%) = 278 (21, M+), 263 (19), 249 (40), 179 (41), 141 (39), 113 (100), 83 (20), 55 (31).
RT 42,03'
MS: m/e (%) = 278 (29, M+), 263 (22), 249 (55), 209 (40), 179 (49), 141 (42), 113 (100), 83 (21), 55 (31).
RT 42,11'
MS: m/e (%) = 278 (23, M+), 263 (21), 249 (44), 209 (35), 179 (47), 141 (39), 113 (100), 83 (21), 55 (34).
Rt 42,47'
MS: m/e (%) = 278 (29, M+), 263 (21), 249 (51), 209 (37), 179 (47), 141 (44), 113 (100), 83 (21), 55 (26).

EXAMPLE 9

Manufacture of 5-(1'-Ethyl-ethylenedioxy)-isolongifolane 7a/7b/7c/7d 220 g (1 mol) purified ketone mixture 4a/4b from example 2 (purity according to GLC: 4a (77%), 4b (12.8%) [86:15], 270 g (3 mol) 1,2-butandiol, 300 ml cyclohexane, and 1 g p-toluene sulfonic acid were charged into a 1 l three-neck-roundbottom-flask with water separator. The mixture was stirred for 50 hours. After cooling to room temperature it was then neutralized with sodium carbonate solution and water and dried above Na$_2$SO$_4$. After distillation of the solvent at reduced pressure 328 g of light brown oil remained.

A subsequent distillation with a 15 cm Vigreux-column produced 195 g (66.8% theor. yield) 7a/7b/7c/7d; b.p. 2 mm 152°–157° C. as light yellow oil.

GLC/MS: Conditions See Example 2

Rt 42,55'
MS: m/e (%) = 292 (16, M+), 277 (15), 263 (37), 223 (27), 193 (28),155 (26), 127 (100), 83 (13), 55 (43).
Rt 43,37'
MS: m/e (%) = 292 (32, M+), 277 (25), 263 (56), 223 (48), 193 (41), 155 (37), 127 (100), 83 (17), 55 (49).
Rt 43,66'

MS: m/e (%)=292 (19, M+), 277 (19), 263 (42), 223 (45), 193 (34), 155 (28), 127 (100), 83 (13), 55 (50).
Rt 44,29'
MS: m/e (%)=292 (32, M+), 277 (24), 263 (57), 223 (43), 193 (41), 155 (43), 127 (100), 83 (17), 55 (50).

EXAMPLE 10

Manufacture of 5-(1',2'-dimethyl-ethylene dioxy)-isolongifolane 8a/8b/8c/8d 220 g (1 mol) of purified ketone mixture 4a/4b from example 2 (purity according to GLC: 4a (77%), 4b (12.8%) [86:14]; 270 g (3 mol) 2,3-butandiol, 300 ml cyclohexane, and 1 g p-toluene sulfonic acid were charged into a 1 l three-neck-roundbottom-flask and stirred for 50 hours under reflux. After cooling to room temperature it has been neutralized with sodium carbonate solution and water and dried above $Na_2SO_4$. The solvent was distilled at reduced pressure. 275 g light brown raw product remained.

Distillation with a 15 cm Vigreux-column produced 211 g (72.2% theor. yield) 8a/8b/8c/8d; b.p. 2.5 mm 158°-162° C. as a light yellow oil.

D 20/4 = 1,0115
n 20/D = 1,4975
GLC/MS: Conditions see example 2
Rt 39,69'
MS: m/e (%)=292 (41, M+), 277 (25), 263 (57), 223 (50), 193 (49), 155 (50), 127 (100), 83 (20), 55 (29).
Rt 40,14'
MS: m/e (%)=292 (47, M+), 277 (30), 263 (63), 223 (59), 193 (53), 155 (51), 127 (100), 83 (20), 55 (35).
Rt 42,76'
MS: m/e (%)=292 (16, M+), 277 (14), 263 (28), 223 (28), 193 (26), 155 (25), 127 (100), 83 (15), 55 (28).
Rt 43,36'
MS: m/e (%)=292 (56, M+), 277 (40), 263 (91), 223 (78), 193 (66), 155 (64), 127 (100), 83 (38), 55 (41).

EXAMPLE 11

Description of Odours of Ketals 5 to 8

The olfactory qualities of the materials at 10% in Ethanol have been evaluated by a group of experts using smelling strips. Their findings were as follows:

5a/5b [86:14] from example 5b:
strong, sweet-woody, with a velvety-ambra accent and flowery aspects.

5a from example 6:
strongly woody with a mossy ambra-accent and a fresh effect.

5b from example 7:
woody, light flowery, with a softly earthy ambra note, a bit weaker than compound 5a.

6a/6b/6c/6d (from example 8):
strongly woody, powdery, with a fresh ambra accent.

7a/7b/7c/7d (from example 9):
dry, woody

8a/8b/8c/8d (from example 10):
strongly woody, with aspects of mossy, earthy and sweet-animal notes.

The odors of all compounds were found to be extremely longlasting and could be smelled after several weeks.

EXAMPLE 12

Perfume Base of a Flowery-woody Type

| Oil of bergamot | 7.5 |
|---|---|
| Linalool | 4.0 |
| Phenyl ethyl alcohol | 5.0 |
| Benzyl acetate | 2.0 |
| Citronellol | 2.0 |
| Hedione ® (a) | 10.0 |
| Lyral ® (b) | 4.0 |
| Hydroxycitronellal | 2.5 |
| Roseoxide 1 (c) 10% in DPG | 2.5 |
| Hexyl cinnamic aldehyde, alpha | 7.5 |
| Patchouly Oil Indonesian | 4.0 |
| Iso-E-Super ® (b) | 2.0 |
| Vetiveryl acetate | 2.0 |
| Brahmanol ® F (c) | 2.0 |
| Benzcylsalicylat | 2.0 |
| cis-3-Hexenylsalicylat | 1.0 |
| Cedramber ® (b) | 1.0 |
| Musk Xylene | 1.0 |
| Indole 10% in DPG | 0.5 |
| Extract of Opoponax | 0.5 |
| Extract of Oakmoss 50% in DPG | 5.0 |
| | 68.0 |

(a) Firmenich
(b) IFF
(c) DRAGOCO

The perfume base of the indicated formula presents a well balanced flowery-woody character which may be markedly amplified and harmonized by addition of 32 parts of 5a/5b (80:20).

EXAMPLE 13

Perfume Base of the Fougére Type

| Oil of bergamot | 18.0 |
|---|---|
| Oil of Lavandin Super | 15.0 |
| Lilial ® | 10.0 |
| p-anisaldehyde | 3.0 |
| Coumarin | 5.0 |
| Hexyl cinnamic aldehyde, alpha | 20.0 |
| Ambrinol epoxide 10% in DPG | 0.5 |
| Ambroxan ® (d) 10% in DPG | 1.0 |
| Romaryl ® (c) | 10.0 |
| Peppermint oil | 1.0 |
| | 82.5 |

(c) DRAGOCO
(d) Henkel

The perfume base of the indicated formula shows a fresh herbal fougére odor. An addition of 7.5 parts 6a/6b/6c/6d smoothes the composition and puts an accent on the ambra-woody note. Alternatively, an addition of 7.5 parts 8a/8b/8c/8d also smoothes the composition but puts the accent on an animal woody aspect.

EXAMPLE 14

| Oil of Galbanum ED | 0.5 |
|---|---|
| Eugenol | 1.0 |
| Methylionone-gamma | 5.0 |
| cis-3-Hexenylsalicylat | 6.0 |
| Benzyl acetate | 8.0 |
| Lignofix ® (c) | 5.0 |
| Hedione ® (a) | 10.0 |
| Bencylsalicylat | 10.0 |

| -continued | |
|---|---|
| Hexyl cinnamic aldehyde, alpha | 12.0 |
| Phenyl ethyl alcohol | 15.0 |
| | 72.5 |

(a) Firmenich (c) DRAGOCO

The perfume oil of the indicated formula shows a harmonic flowery green character. Alternative addition of either 7.5 parts 5a/5b or 7a/7b/7c/7d produces a very desirable balancing in a very natural effect.

We claim:

1. Cyclic isolongifolanone ketals of the general formula (A) wherein the wavy lines mean $\alpha$- and $\beta$- configuration and R and R' independently mean radicals selected from the group consisting of hydrogen, methyl or ethyl

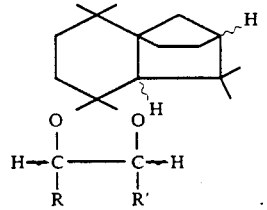

2. Cyclic isolongifolanone ketals as in claim 1, wherein R and R' represent hydrogen.

3. Cyclic isolongifolanone ketals as in claim 1, wherein R represents hydrogen and R' represents methyl, or R represents methyl and R' represents hydrogen.

4. Cyclic isolongifolanone ketals as in claim 1, wherein R represents hydrogen and R' represents ethyl, or R represents ethyl and R' represents hydrogen.

5. Cyclic isolongifolanone ketals as in claim 1, wherein R and R' represent methyl ($\alpha,\beta$).

6. Cyclic isolongifolanone ketals as in claim 1, wherein said ketals are produced by the process comprising obtaining isolongifolene from longifolene, oxidizing isolongifolene to isolongifolene-3-one and reacting with aliphatic 1,2-dioles in an apolar solvent accompanied by separation of water.

* * * * *